United States Patent
Ghosh et al.

(10) Patent No.: US 10,947,474 B2
(45) Date of Patent: Mar. 16, 2021

(54) FRICTION MODIFIER FOR MOTOR OIL

(71) Applicant: Valvoline Licensing and Intellectual Property LLC, Lexington, KY (US)

(72) Inventors: Shibaji Kumar Ghosh, Kolkata (IN); Jesse Dambacher, Lexington, KY (US)

(73) Assignee: VALVOLINE LICENSING AND INTELLECTUAL PROPERTY LLC, Lexington, KY (US)

( * ) Notice: Subject to any disclaimer, the term of this patent is extended or adjusted under 35 U.S.C. 154(b) by 0 days.

(21) Appl. No.: 16/767,691

(22) PCT Filed: Nov. 29, 2018

(86) PCT No.: PCT/US2018/063053
§ 371 (c)(1),
(2) Date: May 28, 2020

(87) PCT Pub. No.: WO2019/108785
PCT Pub. Date: Jun. 6, 2019

(65) Prior Publication Data
US 2020/0385647 A1    Dec. 10, 2020

Related U.S. Application Data

(60) Provisional application No. 62/592,645, filed on Nov. 30, 2017.

(51) Int. Cl.
*C10M 133/16* (2006.01)
*C07C 233/91* (2006.01)
(Continued)

(52) U.S. Cl.
CPC ......... *C10M 133/16* (2013.01); *C07C 233/91* (2013.01); *C10M 2215/082* (2013.01);
(Continued)

(58) Field of Classification Search
CPC ........... C10N 2030/06; C10N 2030/18; C10N 2030/04; C10N 2030/12; C10N 2030/02;
(Continued)

(56) References Cited

U.S. PATENT DOCUMENTS

| | | |
|---|---|---|
| 4,921,624 A | 5/1990 | Kammann, Jr. |
| 5,286,394 A | 2/1994 | Moore |

(Continued)

FOREIGN PATENT DOCUMENTS

EP    1299509 B1    4/2003

OTHER PUBLICATIONS

International Search Report and Written Opinion issued in PCT application No. PCT/US2018/063053, dated Feb. 5, 2019.
(Continued)

*Primary Examiner* — Vishal V Vasisth
(74) *Attorney, Agent, or Firm* — Benesch, Friedlander, Coplan & Aronoff LLP

(57) ABSTRACT

Novel friction reducing additives provide friction modification at a lower effective concentration when added to a motor oil base. A friction reducing motor oil composition may include motor oil base and a friction reducing additive having the structure of the general formula (I):

(Continued)

wherein: $R_1$ is a straight or branched $C_5$-$C_{30}$ alkyl or alkenyl; $R_2$ is H, or a straight or branched alkyl of $C_1$-$C_{10}$; $R_3$ is H, or a straight or branched alkyl of $C_1$-$C_{10}$; P is 0 or $C_1$; n is $C_1$-$C_5$; and m is $C_0$-$C_5$.

20 Claims, 1 Drawing Sheet

(51) Int. Cl.
| | |
|---|---|
| C10N 30/00 | (2006.01) |
| C10N 40/25 | (2006.01) |
| C10N 30/02 | (2006.01) |
| C10N 30/04 | (2006.01) |
| C10N 30/06 | (2006.01) |
| C10N 30/10 | (2006.01) |
| C10N 30/12 | (2006.01) |
| C10N 30/18 | (2006.01) |

(52) U.S. Cl.
CPC ...... *C10N 2030/02* (2013.01); *C10N 2030/04* (2013.01); *C10N 2030/06* (2013.01); *C10N 2030/10* (2013.01); *C10N 2030/12* (2013.01); *C10N 2030/18* (2013.01); *C10N 2030/36* (2020.05); *C10N 2040/255* (2020.05)

(58) Field of Classification Search
CPC .......... C10N 2030/36; C10N 2040/255; C10N 2030/10; C07C 233/91; C10M 133/16; C10M 2215/082
See application file for complete search history.

(56) References Cited

U.S. PATENT DOCUMENTS

| | | | |
|---|---|---|---|
| 5,320,768 | A | 6/1994 | Gutierrez et al. |
| 6,410,597 | B1 | 6/2002 | Bieberich et al. |
| 6,750,185 | B2 | 6/2004 | Ryu et al. |
| 7,438,731 | B2 | 10/2008 | Watanabe et al. |
| 8,148,306 | B2 | 4/2012 | Bartley et al. |
| 8,901,328 | B2 | 12/2014 | Suen et al. |
| 9,193,932 | B2 | 11/2015 | Loper |
| 9,227,920 | B2 | 1/2016 | Suen et al. |
| 9,447,351 | B2 | 9/2016 | Jung et al. |
| 9,487,728 | B2 | 11/2016 | Lundgren |
| 9,499,762 | B2 | 11/2016 | Loper et al. |
| 9,550,955 | B2 | 1/2017 | Loper et al. |
| 9,562,207 | B2 | 2/2017 | DeBlase et al. |
| 10,072,230 | B2 | 9/2018 | DeBlase |
| 2007/0155631 | A1* | 7/2007 | Muir .................... C10M 159/22 508/185 |
| 2010/0006049 | A1* | 1/2010 | Jung ....................... C10L 10/00 123/1 A |
| 2010/0210487 | A1 | 8/2010 | DeBlase et al. |
| 2014/0179571 | A1 | 6/2014 | Loper et al. |
| 2016/0208187 | A1* | 7/2016 | Scanlon ............... C10M 133/06 |
| 2016/0251591 | A1 | 9/2016 | DeBlase et al. |

OTHER PUBLICATIONS

International Preliminary Report on Patentability issued in PCT application No. PCT/US2018/063053, dated Jun. 11, 2020.
Extended European Search report issued in European patent application No. 18883622.5 dated Aug. 27, 2020.

* cited by examiner

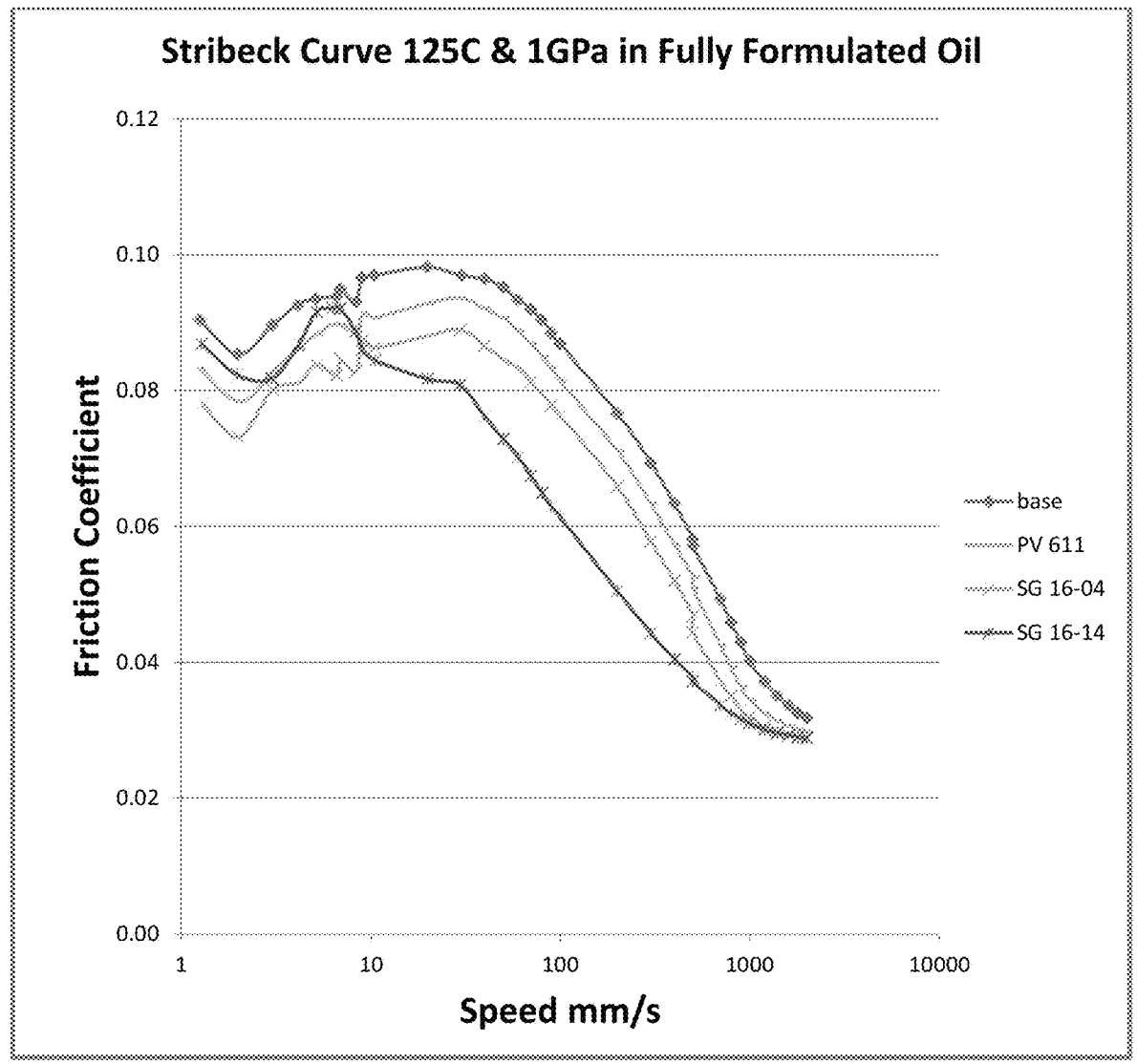

FRICTION MODIFIER FOR MOTOR OIL

RELATED APPLICATIONS

This application is a § 371 U.S. National Stage of International Application PCT/US18/63053, filed Nov. 29, 2018, which claims the benefit of U.S. Provisional Application No. 62/592,645, filed Nov. 30, 2017, the entire content of which are incorporated by reference herein in their entirety.

BACKGROUND

Reducing friction in an automobile engine is one of the important contributors to increasing fuel economy. As the push for higher fuel economy vehicles continues, friction modifiers play an essential function for improving motor oil performance. Improving motor oil performance can lead to better fuel economy and reduce wear and tear on metal components of engines.

Fatty acids and their derivatives are known as fuel and lubricant additives. However, it would be beneficial to provide a new oil additive that is effective at lower concentrations and can be manufactured economically.

SUMMARY

The friction reducing additives described herein provide friction modification at a low effective concentration when added to a motor oil base.

In one embodiment, a friction reducing motor oil composition includes a) motor oil base; and b) a friction reducing additive having the structure of the general formula (I):

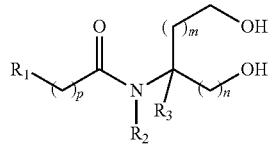

wherein, $R_1$ is a straight or branched $C_5$-$C_{30}$ alkyl or alkenyl; $R_2$ is H, or a straight or branched alkyl of $C_1$-$C_{10}$; $R_3$ is H; or a straight or branched alkyl of $C_1$-$C_{10}$; P is 0 or $C_1$; n is $C_1$-$C_5$; and m is $C_0$-$C_5$.

In another embodiment, a friction reducing additive of the general formula I wherein: $R_1$ is a straight chain $C_{16}$-$C_{18}$ alkyl or $R_1$ is a $C_{16}$ straight alkenyl that may be unsaturated between $C_9$ and $C_{10}$; $R_2$ is H; $R_3$ is $C_1$; P is $C_1$; n is $C_1$; and m is 0 is provided. A friction reducing motor oil additive that is of the general formula I wherein: $R_1$ is $C_{16}$ straight alkenyl that may be unsaturated between $C_9$ and $C_{10}$; $R_2$ is $C_4$; $R_3$ is H; P is $C_1$; n is $C_1$; and m is $C_1$ is also provided.

In yet another embodiment, the friction reducing additive has the structure of the formula (II):

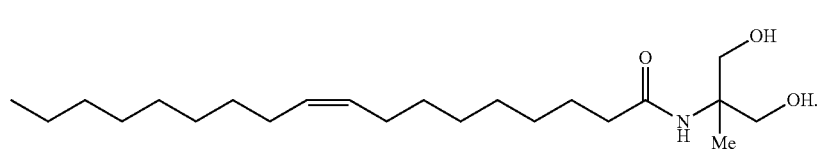

SG-2016-04

And in another embodiment, the friction reducing additive has the structure of the formula (III):

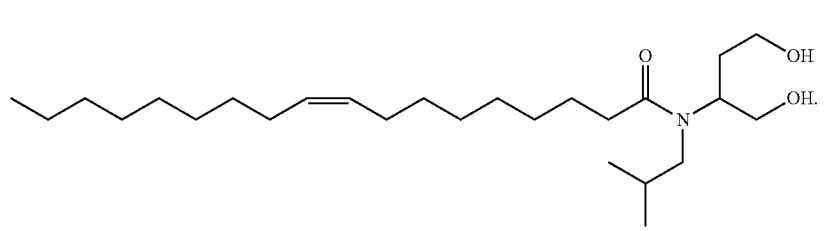

SG-2016-04

The friction reducing additive may also be a combination of additives having the Formulas I, II, III, or any combination of Formula I, II, and III. Further, a friction reducing additive that is a combination of the additive of Formulas I, II, or any combination of Formula I, II, and III together with other commercially available friction reducing additives is provided.

The friction reducing motor oil composition may also include one or more additional additives selected from dispersants, detergents, antioxidants, anti-wear agents, viscosity modifiers, pour point depressants, other friction modifiers, corrosion inhibitors, anti-foamants, demulsifiers, and seal swell agents.

In addition one embodiment, the motor oil base may be present in an amount from about 50% to about 99.9 wt % and the friction reducing additive may be present in an amount from about 0.001 wt % and up to about 5.0 wt % of the total composition of the friction reducing motor oil. In other embodiments, the friction reducing additive may be present in an amount from about 0.001 wt % to about 0.6 wt % of the total composition of the friction reducing motor oil.

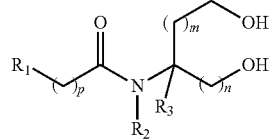

wherein: $R_1$ is a straight or branched $C_5$-$C_{30}$ alkyl or alkenyl; $R_2$ is H, or straight, or branched alkyl of $C_1$-$C_{10}$; R3 is H, or straight or branched alkyl $C_1$-$C_{10}$; n is $C_1$-$C_5$, m is $C_0$-$C_5$.

Preferably, $R_1$ is a straight chain $C_5$-$C_{30}$ alkyl group. Even more preferably, $R_1$ is a straight chain $C_{16}$-$C_{18}$ alkyl group. The straight chain alkyl group of $R_1$ may be saturated or unsaturated. The straight chain alkyl group of $R_1$ may be unsaturated at one position or more than one position.

In one embodiment, a compound of Formula II, is provided:

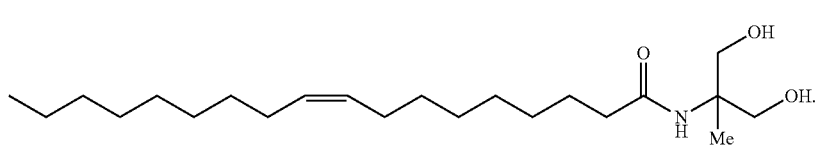

SG-2016-04

BRIEF DESCRIPTION OF THE DRAWINGS

In the accompanying figures, chemical formulas, chemical structures, and experimental data are given that, together with the detailed description provided below, describe example embodiments of the claimed invention.

FIG. 1 is a Stribeck Curve comparing the Friction Coefficient for motor oils formulated with additives.

DETAILED DESCRIPTION

The friction reducing motor oil additives include novel fatty 2-amido-dialcohol compounds that provide better friction reducing behavior compared to well-known friction modifiers.

In one embodiment, a compound of Formula I, is provided:

Formula II is a variation of formula I wherein: $R_1$ is $C_{16}$; $R_2$ is H; $R_3$ is $C_1$; P is $C_1$; n is $C_1$; and m is 0. In formula II, the straight chain alkenyl group of $R_1$ is unsaturated between $C_9$ and $C_{10}$ In one embodiment, a compound of Formula III is provided:

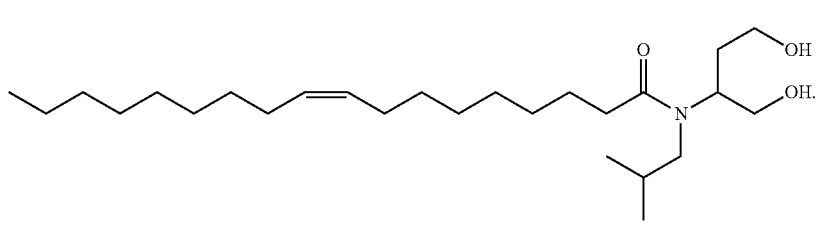

SG-2016-04

Formula III is a variation of formula I wherein $R_1$ is $C_{16}$; $R_2$ is $C_4$; $R_3$ is H; P is $C_1$; n is $C_1$; and m is $C_1$. In formula III, the straight chain alkenyl group of $R_1$ is unsaturated between $C_9$ and $C_{10}$.

The friction reducing additive may comprise Formulas I, II, III, or any combination of Formula I, II, and III; may consist essentially of Formulas I, II, III, or any combination of Formula I, II, and III; or may consist of Formulas I, II, III, or any combination of Formula I, II, and III.

Motor oils may comprise the friction reducing motor oil additive of Formula I, II, III, or a combination of one or more of these additives; may consist essentially of the friction reducing motor oil additive of Formula I, II, III, or a combination of one or more of these additives; or may consist of the friction reducing motor oil additive of Formula I, II, III, or a combination of one or more of these additives.

Further, motor oils may comprise, consist essentially of or consist of a motor oil base, an additive of the Formula I, II, III, or any combination of Formula I, II, and III, and dispersants, detergents, antioxidants, anti-wear agents, viscosity modifiers, pour point depressants, other friction modifiers, corrosion inhibitors, anti-foamants, demulsifiers, and seal swell agents.

In general, one advantage of the friction reducing motor oil additive is that it is effective in small amounts. Preferably a motor oil will contain between about 0.001 wt % and about 5 wt %; between about 0.001 wt % and about 2 wt %; preferably between about 0.5 wt % and about 1.0 wt %; and most preferably between about 0.001 wt % and about 0.6 wt % of the friction reducing motor oil additive. The motor oil may also contain a wt % of friction reducing motor oil additive of any single number found within the range between about 0.001 wt % and about 5 wt %, for example, 0.5 wt %.

Another advantage of the friction reducing motor oil additive is that it is compatible with other motor oil additives. For example, a motor oil that already contains dispersants, detergents, antioxidants, anti-wear agents, viscosity modifiers, pour point depressants, other friction modifiers, corrosion inhibitors, anti-foamants, demulsifiers, or seal swell agents can be used as the motor oil for addition of the inventive friction reducing motor oil additive.

The dispersants, detergents, antioxidants, anti-wear agents, viscosity modifiers, pour point depressants, other friction modifiers, corrosion inhibitors, anti-foamants, demulsifiers, or seal swell agents are used in amounts generally encountered in the art, for example between about 0.01% and about 5% (see U.S. Pat. No. 9,562,207, for example). The motor oil may also contain a wt % of additive of any single number found within the range between about 0.01 wt % and about 5 wt %, for example, 1.0 wt %, 2.0 wt % or 5.0 wt %.

Yet another advantage of the friction reducing motor oil additive is that it is compatible with any type of oil where friction reduction is desired. The friction reducing motor oil additive can be added to fully synthetic or partially synthetic or any commercially available motor oil. Generally, the motor oil will be largest ingredient in the final composition. The motor oil will be present in an amount between about 50 wt % to about 99.9 wt %. The motor oil base may also contain a wt % of motor oil of any single number found within the range between about 50 wt % and about 99.9 wt %, for example, 95.5 wt %.

A motor oil containing the friction reducing motor oil additive will reduce friction in both boundary and mixed regime where gap between metal to metal is very narrow, which is important for getting better fuel economy.

EXAMPLES

Certain embodiments are described below in the form of examples. While the embodiments are described in considerable detail, it is not the intention to restrict or in any way limit the scope of the appended claims to such detail, or to any particular embodiment.

Example 1: Synthesis of Exemplary Compound

While any appropriate synthesis of compounds of the formula I, II or III are encompassed by the invention, one scheme for synthesis of a compound of the formula III (SG-2016-14) will be described.

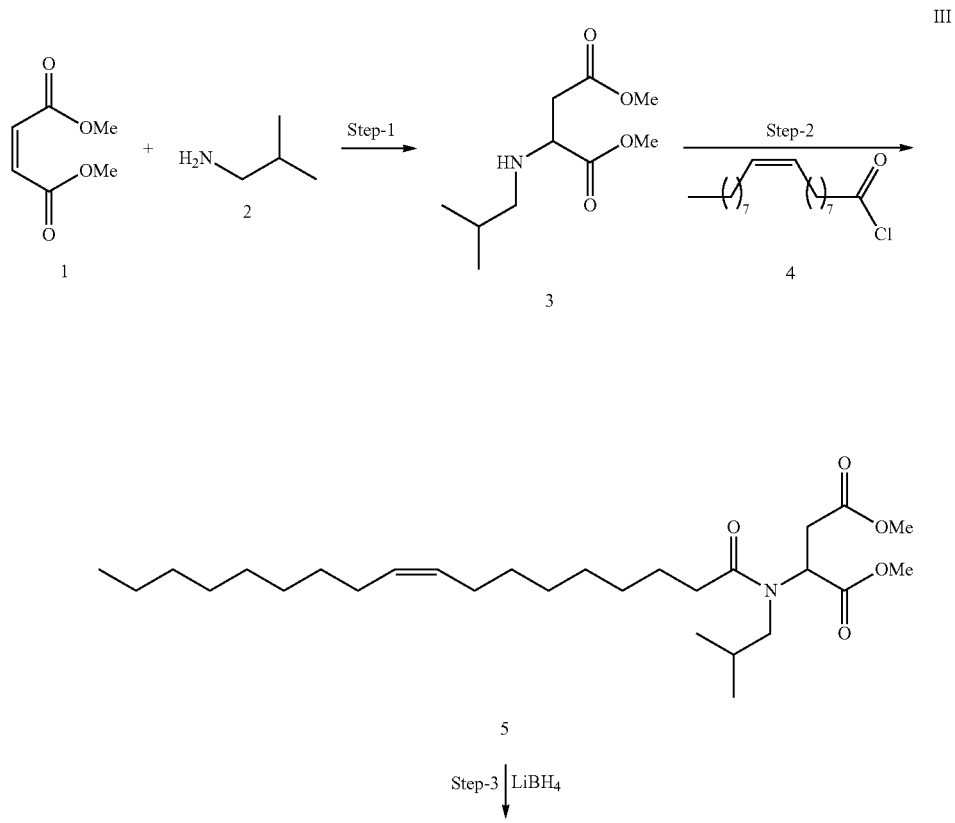

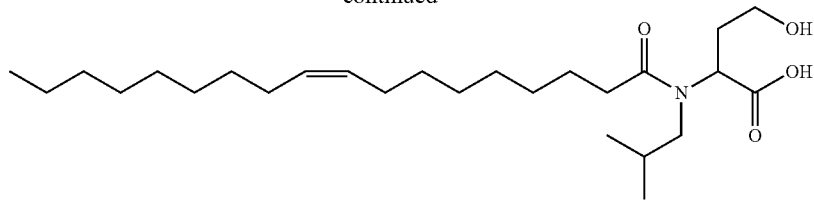

SG-2016-14

Step-1: To compound 1 (10.0 g, 69.38 mmol) was added isobutylamine (2) (6.09 g, 83.26 mmol) dropwise at 26° C. while stirring the mixture under nitrogen atmosphere. After complete addition, the reaction mixture was allowed to stir for 16 hours at 26° C. under nitrogen atmosphere. After 16 hours of stirring, excess isobutylamine was removed under reduced pressure as much as possible to get a crude product which was purified using silica gel (Eluent: 50% ethyl acetate/hexane) to afford a pure compound 3 (13.0 g, 87%).

Step-2: To a stirring solution of compound 3 (13.0 g, 59.8 mmol) in dichloromethane (100 mL) was added triethylamine (12.5 mL, 89.7 mmol) and oleic acid chloride 4 (freshly prepared by known method) (18.0 g, 59.8 mmol) dropwise at 26° C. under nitrogen atmosphere. The reaction mixture was allowed to stir for 15 hours at 26° C. under nitrogen atmosphere. After 15 hours of stirring, 1M HCl was added to the mixture and stirred for 15 minute then extracted with dichloromethane. The organic layer was dried over $Na_2SO_4$, concentrated under reduced pressure to get a crude product which was purified using silica gel (Eluent: 20% Ethyl acetate/hexane) to afford a pure compound 5 (20.8 g, 72%).

Step-3: To a stirring solution of compound 5 (7.0 g, 14.53 mmol) in dry THF (70 mL) was added $LiBH_4$ (635 mg, 29.15 mmol) portionwise at 0° C. under nitrogen atmosphere and the reaction mixture was allowed to stir for 15 hours at 26° C. After complete consumption of the starting material MeOH was added slowly at 0° C. under nitrogen atmosphere until a clear solution was formed and then the solvent was evaporated to get a crude material. 1M HCl was added to the crude viscous material and then extracted with Ethyl acetate. The organic layer was dried over $Na_2SO_4$, concentrated under reduced pressure to get a crude product which was purified using silica gel (Eluent: 60% Ethyl acetate/hexane) to afford a pure compound SG-2016-14, or Formula III, (4.0 g, 65%).

Example 2: Production and Analysis of Motor Oil with Formula II and III as an Additive As can be seen in FIG. 1, motor oils containing either formula II or III additive are compared with previously produced motor oils PV611 and an additive free motor oil base. Motor oils with the additive of either formula II or formula III showed enhanced friction reduction over the motor oil base and the previously available friction reducing formulated oil, PV611. The additives are effective at a concentration of 0.5 wt %.

The performance of motor oils containing Formula II and III as additives was compared to a PV611 and a motor oil with no additive in a corrosion test. The Results are shown in Table 1:

| ADDITIVE | | | | |
|---|---|---|---|---|
| | None | PV611 | Formula II | Formula III |
| Cu, ppm | 5 | 5 | 11 | 7 |
| Pb, ppm | 29 | 71 | 142 | 87 |

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11. The term wt % is meant to describe a comparison of the weight of one compound to the weight of the whole composition expressed as a percent. It can also be described as wt. %, or (w/w) %. Motor oil includes oil used to lubricate any type of motor or machine where an oil is used. The straight chain alkyl or alkenyl groups described herein may also be referred to as fatty acids, fatty acyls, or fatty acids chains.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A friction reducing motor oil additive, wherein the additive has the structure of the general formula (I):

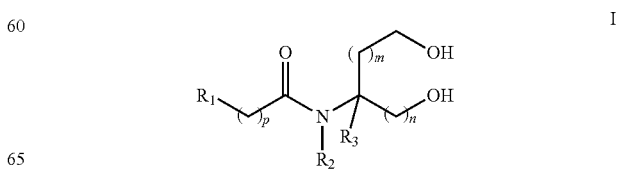

I wherein, $R_1$ is straight or branched $C_5$-$C_{30}$ alkyl, or alkenyl; $R_2$ is H, or a straight or branched alkyl of $C_1$-$C_{10}$; $R_3$ is H, or a straight or branched alkyl of $C_1$-$C_{10}$; P is 0 or $C_1$; n is $C_1$-$C_5$; and m is $C_0$-$C_5$ and wherein the additive is present in an amount between about 0.001 wt % and about 5 wt %.

2. The friction reducing motor oil additive of claim 1, wherein $R_1$ is straight chain $C_{16}$-$C_{18}$ alkyl.

3. The friction reducing motor oil additive of claim 1, wherein: $R_1$ is a $C_{16}$ straight alkenyl; $R_2$ is H; $R_3$ is $C_1$; P is $C_1$; n is $C_1$; and m is 0.

4. The friction reducing motor oil additive of claim 3, wherein $R_1$ is unsaturated between $C_9$ and $C_{10}$.

5. The friction reducing motor oil additive of claim 1, wherein: $R_1$ is $C_{16}$ straight alkenyl; $R_2$ is $C_4$; $R_3$ is H; P is $C_1$; n is $C_1$; and m is $C_1$.

6. The friction reducing motor oil additive of claim 5, wherein $R_1$ is unsaturated between $C_9$ and $C_{10}$.

7. The friction reducing motor oil additive of claim 1, wherein the additive has the structure of the formula (II):

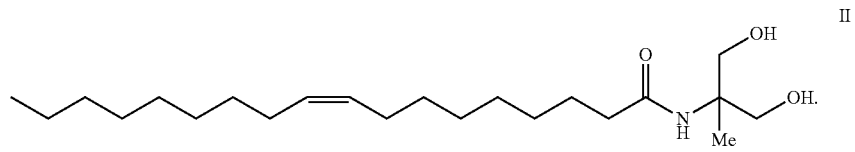

SG-2016-04

8. The friction reducing motor oil additive of claim 1, wherein the additive has the structure of the formula (III):

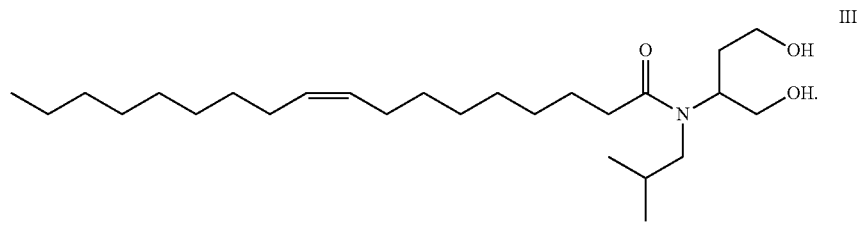

SG-2016-04

9. The friction reducing motor oil additive of claim 1, wherein the additive is a combination of additives having the general Formula I, II or III.

10. A friction reducing motor oil composition comprising:
a) motor oil base; and
b) a friction reducing additive having the structure of the general formula (I):

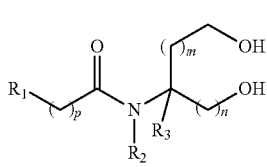

wherein: $R_1$ is a straight or branched $C_5$-$C_{30}$ alkyl or alkenyl; $R_2$ is H, or a straight or branched alkyl of $C_1$-$C_{10}$; $R_3$ is H, or a straight or branched alkyl of $C_1$-$C_{10}$; P is 0 or $C_1$; n is $C_1$-$C_5$; and m is $C_0$-$C_5$.

11. The friction reducing motor oil composition of claim 10, wherein $R_1$ is straight chain $C_{16}$-$C_{18}$ alkyl.

12. The friction reducing motor oil composition of claim 10, wherein: $R_1$ is a $C_{16}$ straight alkenyl; $R_2$ is H; $R_3$ is $C_1$; P is $C_1$; n is $C_1$; and m is 0.

13. The friction reducing motor oil composition of claim 12, wherein $R_1$ is unsaturated between $C_9$ and $C_{10}$.

14. The friction reducing motor oil composition of claim 10, wherein: $R_1$ is $C_{16}$ straight alkenyl; $R_2$ is $C_4$; $R_3$ is H; P is $C_1$; n is $C_1$; and m is $C_1$.

15. The friction reducing motor oil composition of claim 14, wherein $R_1$ is unsaturated between $C_9$ and $C_{10}$.

16. The friction reducing motor oil composition of claim 10, wherein the friction reducing additive has the structure of the formula (II):

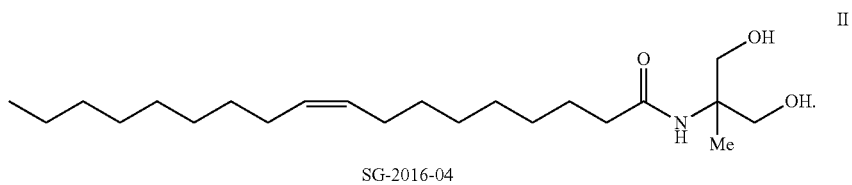 [SMILES: CCCCCCCC/C=C\CCCCCCCC(=O)NC(C)(CO)CO]

SG-2016-04

17. The friction reducing motor oil composition of claim 10, wherein the friction reducing additive has the structure of the formula (III):

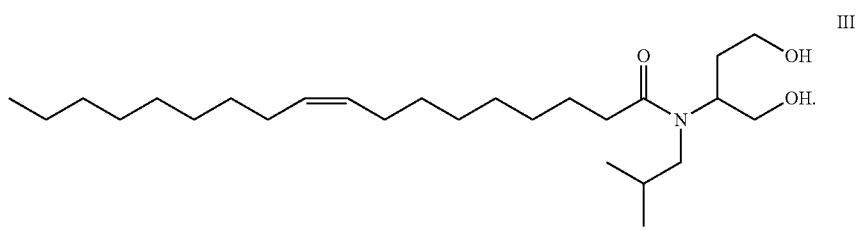

SG-2016-04

18. The friction reducing motor oil composition of claim 10, wherein the friction reducing additive is a combination of additives having the general Formula I, II or III.

19. The friction reducing motor oil composition of claim 10, wherein the composition further comprises one or more additional additives selected from the group consisting of: dispersants, detergents, antioxidants, anti-wear agents, viscosity modifiers, pour point depressants, other friction modifiers, corrosion inhibitors, anti-foamants, demulsifiers, and seal swell agents.

20. The friction reducing motor oil composition of claim 10, wherein the motor oil base is present in an amount from about 50% to about 99.9 wt % and the friction reducing additive is present in an amount from about 0.001 wt % to about 5.0 wt % of the total composition of the friction reducing motor oil.

* * * * *